(12) United States Patent
Harding et al.

(10) Patent No.: US 9,044,613 B2
(45) Date of Patent: Jun. 2, 2015

(54) TRANSCUTANEOUS ELECTRICAL STIMULATION WAVEFORM GENERATOR AND METHOD OF USE

(71) Applicants: Douglas C. Harding, Orem, UT (US); Alma Ray Ivie, Orem, UT (US); Richard J. Ivie, Orem, UT (US)

(72) Inventors: Douglas C. Harding, Orem, UT (US); Alma Ray Ivie, Orem, UT (US); Richard J. Ivie, Orem, UT (US)

( * ) Notice: Subject to any disclaimer, the term of this patent is extended or adjusted under 35 U.S.C. 154(b) by 0 days.

(21) Appl. No.: 14/073,466

(22) Filed: Nov. 6, 2013

(65) Prior Publication Data
US 2014/0188190 A1 Jul. 3, 2014

Related U.S. Application Data

(60) Provisional application No. 61/722,945, filed on Nov. 6, 2012.

(51) Int. Cl.
*A61N 1/00* (2006.01)
*A61N 1/36* (2006.01)
*A61N 1/04* (2006.01)

(52) U.S. Cl.
CPC ........... *A61N 1/36125* (2013.01); *A61N 1/0492* (2013.01); *A61N 1/36014* (2013.01); *A61N 1/36025* (2013.01); *A61N 1/0456* (2013.01)

(58) Field of Classification Search
CPC ............ A61N 1/36125; A61N 1/0456; A61N 1/36025; A61N 1/36014; A61N 1/0492
USPC .......................................... 607/59
See application file for complete search history.

(56) References Cited

U.S. PATENT DOCUMENTS

2006/0241719 A1* 10/2006 Foster et al. ..................... 607/45
2010/0160998 A1* 6/2010 Bell ................................ 607/46

* cited by examiner

*Primary Examiner* — Robert N Wieland
(74) *Attorney, Agent, or Firm* — J. Todd Rushton

(57) ABSTRACT

A transcutaneous waveform generator capable of producing a therapeutic shaped wave that may be administered to the user without perception of electrical stimulation.

15 Claims, 7 Drawing Sheets

TRANSCUTANEOUS ELECTRICAL STIMULATION WAVEFORM GENERATOR AND METHOD OF USE

The present application is related and claims priority to U.S. Provisional Patent Application No. 61/722,945, filed Nov. 6, 2012. The disclosure therein, incorporated by reference.

DEFINITIONS

TCES or Transcutaneous Cranial Electrical Stimulation is the process of applying a low frequency envelope containing high-frequency balanced current pulses to the head which potentiates any drug that may be in the body and lowers opiate requirements.

The Limoge waveform is the specific waveform generated by the TCES process which was identified by Dr. Aime Limoge and consists of a low frequency electrical envelope, of 4 ms on and 6 ms off, containing high-frequency balanced, zero net charged pulses. For the purpose of this disclosure the terms Limoge waveform and TCES waveform are considered synonymous and may be used interchangeably.

Electroanesthesia is a means of using electricity to produce an anesthetic effect.

Pure electroanesthesia is electroanesthesia without the addition of tranquilizers, barbiturates, neuroleptics, and curare like drugs.

Hysteresis is a characteristic of a ferromagnetic material when it is magnetized in one direction, it will not relax back to zero magnetization when the imposed magnetizing field is removed. It must be driven back to zero by a field in the opposite direction.

A hysteresis loop is formed when an alternating magnetic field is applied to ferromagnetic material, its magnetization will trace out a loop called a hysteresis loop.

Cranial electrical stimulation (CES) is a psychiatric treatment that applies a small, pulsed electric current across a patient's head. It is similar to TCES but with different waveforms and resulting therapeutic results.

Deep brain stimulation is another form of cranial stimulation that physically implants electrodes into the brain instead of using surface electrodes.

BACKGROUND

In 1957 a group of French Scientists led by Dr. Aime Limoge began a research project involving Electroanesthesia which is a means of using electricity to produce an anesthetic effect. They experimented for 5 years trying to eliminate convulsions induced by using enough electricity to produce the anesthetic effect. In 1964 they tried a combination of low frequency rectangular wave currents combined with the high frequencies, and received the desired effect. The Limoge Wave, which is better known as Transcutaneous Cranial Electrical Stimulation (TCES), was discovered.

On Sep. 27, 1971 The Limoge Wave technique was demonstrated at the United States Army Institute of Dental Research at Walter Reed Army Medical Center. The Conference was hosted by Colonel Robert M. Johnson Chief of Dental Research, and by General Surindar N. Bhaskar. As a result of this conference, Limoge was awarded a contract with the USAMRDC which represented the introduction of the Limoge TCES Wave to the United States.

Since then many research studies have been published supporting TCES and its benefits for not only anesthesia but many other neurological disorders such as anxiety, depression, and drug rehabilitation. Although TCES has had limited use in hospitals in France since 1971, this technology has not be introduced into the United States nor utilized worldwide to its full potential because of technical difficulties such as, patients having a perceived electrical shock due to an underlying DC component in the stimulus output and the medical community not fully understanding or appreciating the potential of this device.

Several individual devices have been constructed for research purposes but no one has been able to successfully replicate the Limoge wave into a device that totally eliminates the DC component, is easily manufactured, and meets the specific requirements needed to treat the several disorders that have been recognized.

SUMMARY OF THE INVENTION

Dr. Limoge recognized that technological improvements in electronics would allow his waveform to become more efficient, stating; "I believe that although it is not yet ready to become a part of general practice, pure general electroanesthesia is possible . . . continued efforts in neurophysiologic and biochemical research, combined with progress in electronics, certainly will provide the answers to the mechanism of action of electric current and provide resolution to the problems" *An Introduction to Electroanesthesia*, Limoge, pg. 94. The present invention is a combination of several innovative solutions that have been formulated as a result of additional research and particularly from state of the art electronics and materials.

One embodiment of the present invention comprises creating a stimulus waveform with no DC components resulting in the absence of any electrical sensation perceived by the user as the intensity of the TCES currents are increased to required therapeutic levels of intensity; including isolation of the TCES waveform from the power source whether the power input is alternating current or direct current.

One embodiment of the present invention or TCES waveform generator includes providing TCES waveform startup timing in such a way to prevent any shock or unpleasant sensation to the patient.

One embodiment of the present invention or TCES waveform generator includes the waveform, its shape and timing, necessary to provide the desired therapeutic outcome for the patient.

Another embodiment of the present invention includes suppression of portions of the output signal that eliminates unwanted and unnecessary high frequency elements of the TCES waveform.

A final embodiment of the present invention or TCES waveform generator includes the application of the device to the patient or the transfer of energy from the TCES waveform generator to the patient or user including, connection of the electrical leads and electrodes to the individual and the TCES waveform generator, placement of the electrodes, type, size, shape and material used to maximize the TCES waveform and effect and provide and optimal connection to the patient.

BRIEF DESCRIPTION OF THE DRAWINGS

The following description of the embodiments can be understood in light of the Figures, which illustrate specific aspects of the embodiments and are part of the specification. Together with the following description, the Figures demonstrate and explain the principles of the embodiments. In the Figures the physical dimensions of the embodiment may be

DETAILED DESCRIPTION

Figure 1:
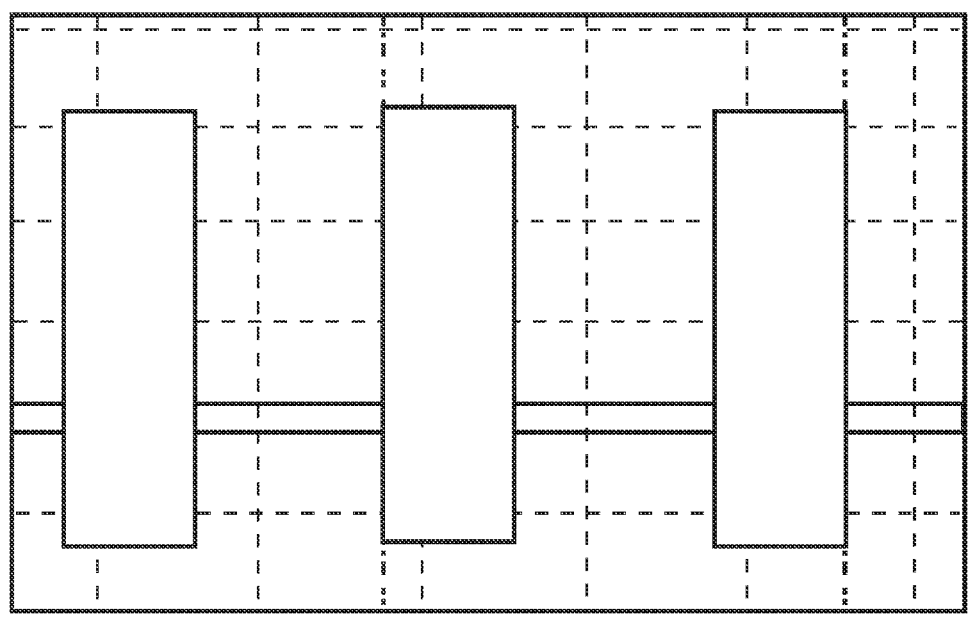
FIG. 1 is one embodiment of the stimulation waveform.
Figure 2:
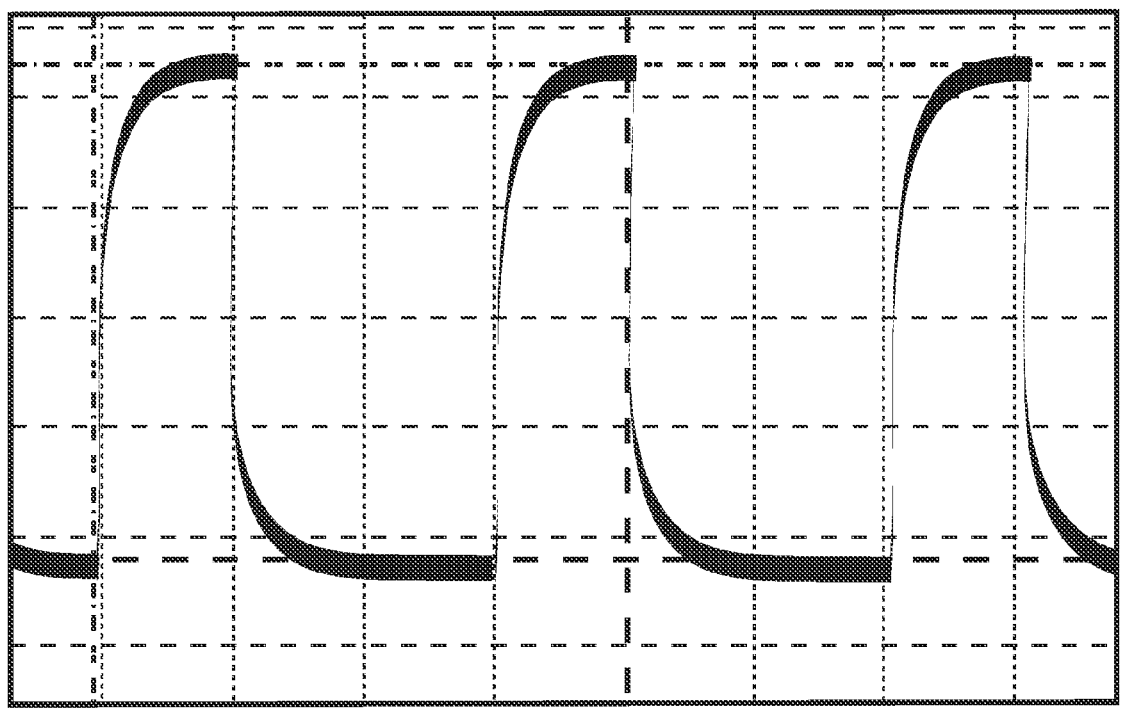
FIG. 2 is one embodiment of the shaped stimulation waveform.

The conventional Limoge waveform consists of gated high frequency pulses as shown in FIGS. 1 and 2. The high frequency waveform and gating frequencies of the Limoge waveform were determined by him over the years to optimize the therapeutic value of the signals. This invention includes the waveforms created by Dr. Limoge exactly as he had envisioned but was unable to create. The waveform created by Dr. Limoge with the additions of current technology and systems added by the inventors is critical to this invention and the benefits it will give to the patient. The waveform described in this invention and demonstrated in FIGS. 1 & 2 represent, the waveform submitted as part of this invention.

Figure 3:
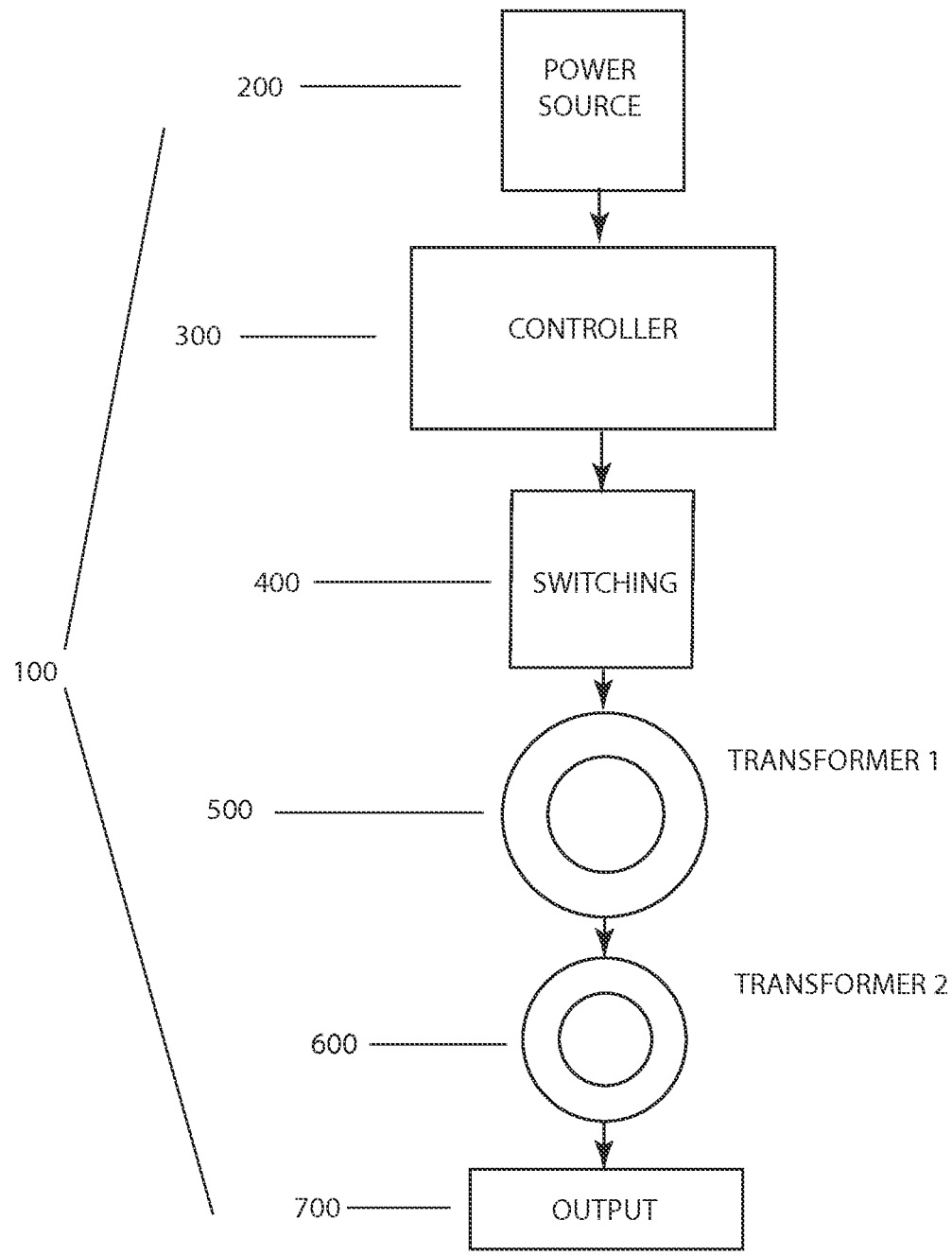
FIG. 3 is one embodiment of the waveform generator.

The TCES waveform generator of the present invention contains electrical/electronic circuitry that is used to generate the Limoge waveform. It consists of the major electrical components shown in FIG. 3 that can be combined into a single stand-alone waveform generator unit or a combination of two or more interconnected units linked together to accomplish the waveform generator 100. The power source 200 can be from a direct current (DC) source such as a battery or an alternating current (AC) source such as common household power. The controller 300 can be a microprocessor, field programmable gate array (FPGA), solid state electronics, or any computer or computer like source that can generate the timing and logic necessary to create the TCES waveform. Switching circuitry 400 is an electronic component or components necessary to react to the signals created by the controller and match the transfer to the transformer. The primary transformer or transformer 1 500 converts the digital portion of the TCES waveform into the analog TCES waveform and provides isolation from the power source and any DC levels, that are, or may be associated, with the generation of the TCES waveform. The windings of the transformer and transformer material are selected to produce optimum power transfer and ratio of the positive and negative portions of the TCES waveform. Transform 2 600 eliminates the high frequency components of the TCES waveform, thus transforming the shape of the positive and negative going portions of the waveform to match the desired shape required by Dr. Limoge. The output 700 is the interface between the TCES waveform generator and the patient. It includes the cabling or patient interface including the electrodes that attach to the patient, which is normally the head but could be connected in other locations of the body.

Each of these components is critical in creating the desired TCES waveform and removing the DC component. By correctly generating the TCES waveform as described, the output is completely isolated from the input signals to the transformer. Limoge identified that both positive and negative going signals (AC) are much more beneficial than DC signals. Further he concluded that the waveform should not be symmetrical but has a shape where the positive portion of the signal is ⅔ greater than the negative. This can be achieved by moving the reference output voltage from 0.0 volts and timing the initial waveform by the controller and switching circuitry to match the characteristics of the transformer windings and transformer materials. The energy in the positive portion of the signal is equal to the energy in the negative portion of the signal and there is a net zero output that goes to the patient yet transfers the power necessary to achieve the therapeutic advantages of the TCES waveform.

Dr. Limoge was never able to achieve a perfect ⅔ to ⅓ ratio because of the DC elements of his devices. This problem has been removed in this invention by first removing any DC signals from the output, providing proper timing from the controller and using the characteristics of the transformer to shift its reference to be exactly at the point of ⅔ positive and ⅓ negative.

Further to accomplish the purposes of the present invention it was necessary to select the proper transformer material such that the transformer does not become saturated or introduce a DC component back into the therapeutic waveform output. Therefore the selection of the transformer material is critical and is a part of this invention. The properties of the transformer material were selected based upon the frequency of the switching, the composition of the core material, and the power being introduced to the core material. The most important property considered in the design of the transformer was the requirement to not allow the transformer to either saturate by being over driven by the controlling signals or be under driven which would result in energy being wasted and a reduction of the amount of power transferred to the patient.

Because of the variety of frequencies and power that can be selected to generate the TCES waveform, this invention does not include just a single transformer or switching combination but a variety of options carefully designed based on the properties of the transformer to give maximum power transfer while still preserving the waveform, the ratio of positive and negative portions of the waveform, and the elimination of all DC components in the waveform.

The choice of transformer material used to create the TCES waveform were high permeability ferrite toroids. They were chosen because ferrite toroids offer high magnetic efficiency since there is no air gap and the cross-sectional area is uniform. In addition, high permeability materials such as J materials are engineered for optimum frequency and impedance performance suitable for low-level power transformers as required for the TCES waveforms. Toroids are the least expensive ferrite shape and are available in a variety of sizes, outer diameters of 2.54 mm-140 mm which provide flexibility in future designs of the TCES waveform.

Another major consideration in the construction of the transformer are the windings on the toroid which included the configuration of the windings, the size of wire, and the number of turns necessary to achieve the necessary balance in the TCES waveform. There is not just one combination that is appropriate for all possible waveforms but a variety of combinations depending on the frequency of the waveform, the amount of power being transferred, the voltage level and current being delivered to the transformer from the power source. Although the current configuration consists of three separate windings, other configurations that contribute to future versions of the TCES waveform will also be considered as part of this invention.

Proper shaping of the output high frequency of the TCES waveform has been found to be critical in creating the required signal. Instead of using square wave pulses which is common in other similar devices, the unwanted elements of the TCES waveform are removed by the use of a second transformer that also uses a ferrite toroid.

The output current intensity and frequency of the TCES waveform are controlled by the power source, controller, and transformers which allow for a variety of output levels and frequencies, however, Dr. Limoge specified certain outputs that he determined optimal so only that output which fits his specifications is currently being used. However, through further studies other waveforms may prove to be advantages and these are included in this invention.

Early versions of the TCES waveform generator and other CES or deep brain stimulator devices may create a shock or unpleasant sensation during the use of the device or when being turned ON or OFF. The TCES waveform generator of the present invention removes this issue completely. The elimination of the DC component removes any shock or unpleasant sensation during use; even as the output levels are adjusted to the maximum allowable levels. But to remove any shock or unpleasant sensation during turn ON and OFF was not achieved just by removing the DC component but required additional design which is another feature of this invention.

Typically when using a transformer any allowance of that transformer to become saturated can add a DC component and possibly result in a shock or unpleasant feeling as before described. So the first requirement of the transformer was to not be allowed to go into saturation. This was not a difficult task once the signal has been generated but to avoid saturation when the TCES generator is being turned ON or OFF was difficult. This balance was accomplished by timing of the TCES signal and careful use of the transformer to avoid saturation.

Figure 4:
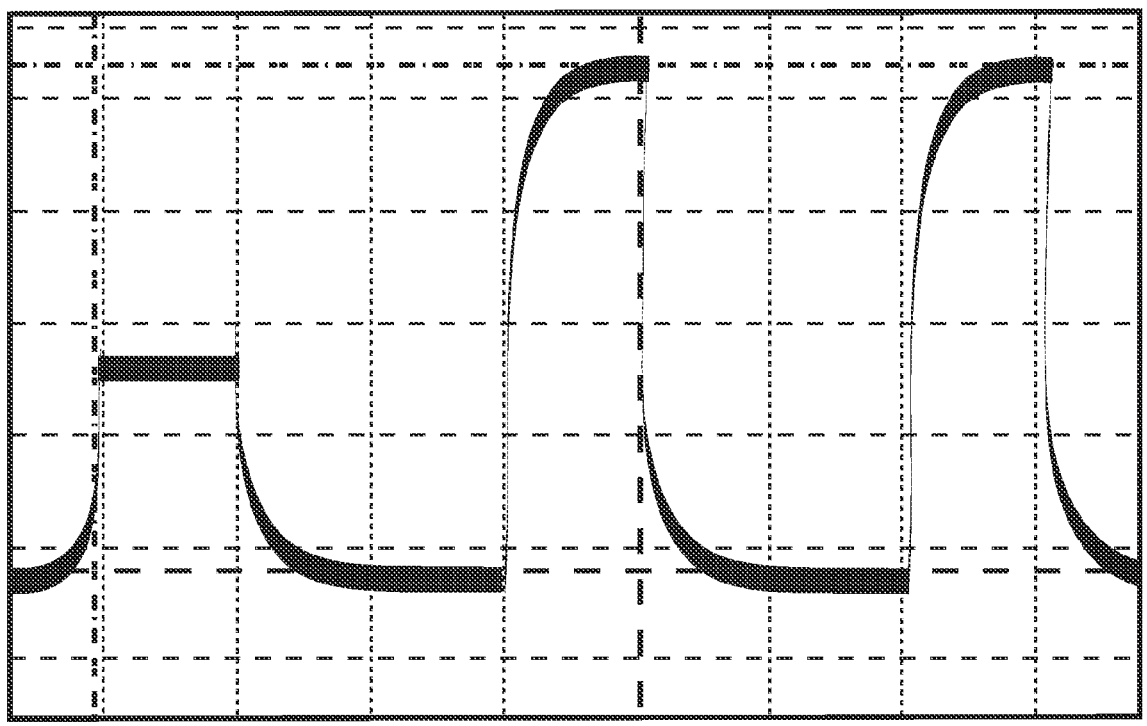
FIG. 4 is one embodiment of the starting stimulation waveform.

When the signal is first sent to the transformer, unless it is controlled, it will saturate. This is because the same amount of energy to maintain the proper levels is less than the energy to initiate or terminate the signal. Since the core material of a transformer is ferromagnetic, it works on the principle of hysteresis. When a ferromagnetic material is magnetized in one direction, it will not relax back to zero magnetization when the imposed magnetizing field is removed. It must be driven back to zero by a field in the opposite direction. If an alternating magnetic field is applied to the material, its magnetization will trace out a loop called a hysteresis loop. If a ferromagnetic material is driven beyond the boundary of the core material, the magnetism will saturate, causing a conflict with the proper hysteresis and the hysteresis loop. The saturation results in distortion of the magnetic signal and creates an unwanted DC component. Saturation will occur with a normal alternating signal if the initial and final pulses are not modified since the beginning of the loop is at the zero axis, not the full hysteresis loop. To resolve this issue with transformer of the present invention, the timing of the hysteresis loop was carefully timed so as at the beginning or conclusion of the gated high frequency signal, the driving magnetic signal is limited to only a portion, which is one embodiment, ⅓ of the full signal which keeps the ferromagnetic core from saturating, see FIG. 4. Once the alternating driving signal conforms to the hysteresis loop, then the full magnetic driving signals can be applied without any saturation. By limiting the initial and final portion of the high frequency signal, saturation was avoided along with any unwanted magnetic and electrical components that can result in a possible shock or unpleasant feeling. The creation of the initial and final partial cycle was accomplished by careful timing and monitoring of the driving signal to determine what part of the gated high frequency is being observed. By doing this it is possible to determine when the partial cycle is necessary to avoid saturation.

Figure 5:
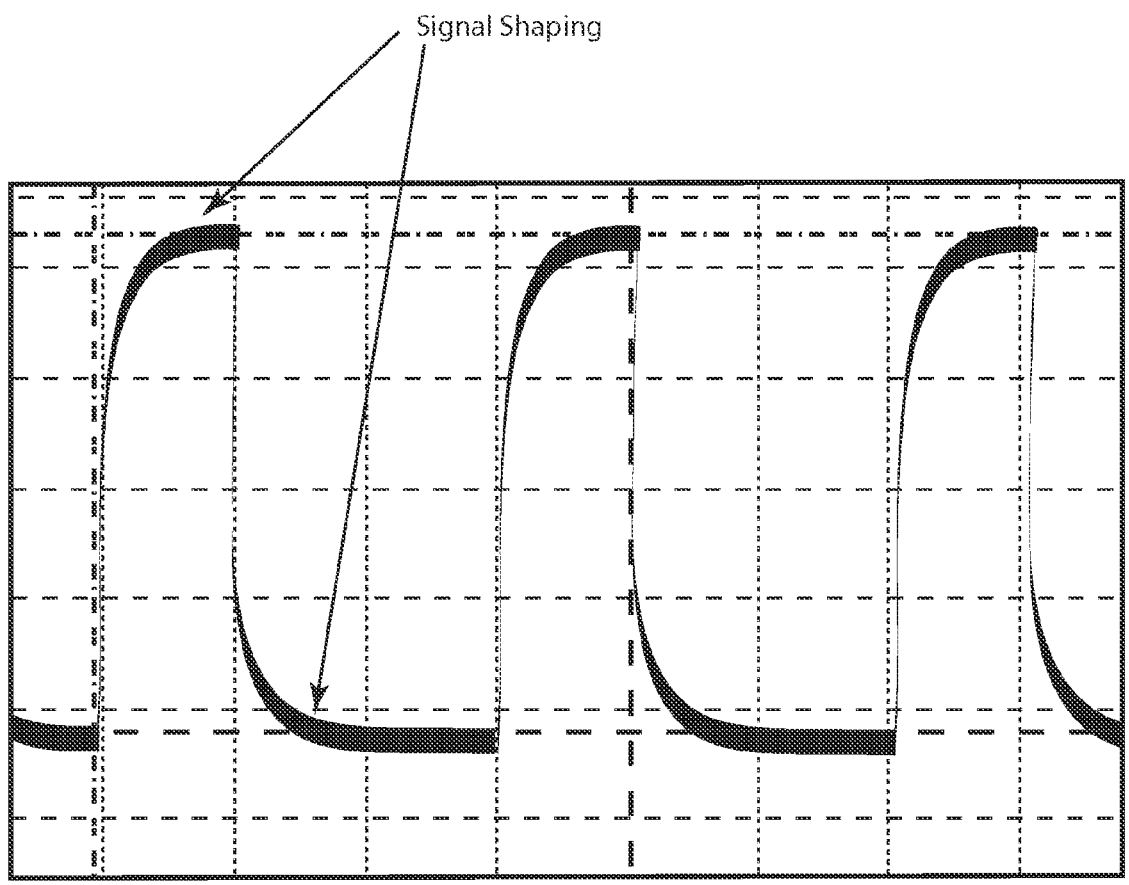
FIG. 5 is one embodiment of the shaped stimulation waveform.

Another element of the TCES waveform generator of the present invention is to eliminate unwanted and unnecessary high frequency elements of the TCES waveform. Dr. Limoge further required a unique shaping of the output waveform to eliminate undesirable frequencies not necessary in transferring the power of the TCES waveform to the patient. This is accomplished with a second transformer using another ferrite toroid that can be adjusted by varying the number of windings on the toroid to shape the waveform from essentially a square wave to a rounded wave which shows a deceleration of amplitude as it approaches the apex in both the positive and negative directions, see FIG. 5. This approach removes the unwanted elements without introducing any DC components.

Figure 6:
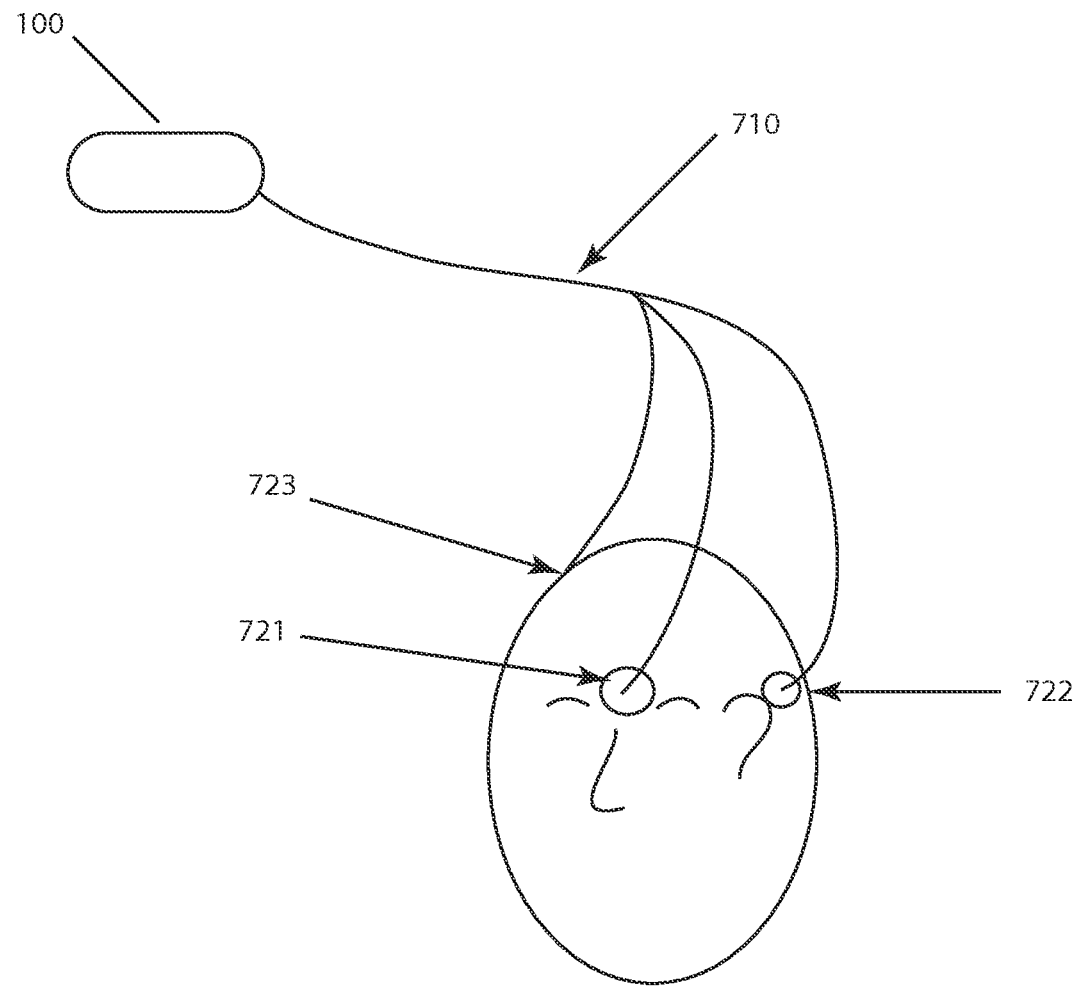
FIG. 6 is one embodiment of the electrode placement for stimulation.
Figure 7A:
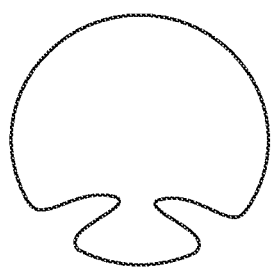
FIGS. 7a, 7b and 7c are embodiments of electrodes.
Figure 7B:
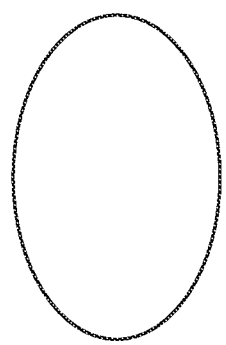
Figure 7C:

FIG. 6 show the final element of the present invention is to transfer the energy from the TCES wave form generator 100 to the patient. Even with the optimum creation of true Limoge TCES waveforms, without proper transfer of that energy from the TCES wave form generator 100 to the patient, the effect on the patient will be minimal. As part of this invention it was necessary to consider in following with regards to the transfer of energy.

Connection of the electrodes 721, 722, 723 to the individual and the TCES waveform generator. High quality shielded wire leads 710 (3 independent strands) is required to connect the patient to the TCES Wave Form Generator 100. It is necessary to avoid any interference from outside electrical radiation as well as be certain that the waveform generator 100 does not emit any undesirable signals.

Location of the electrodes 721, 722, 723 is one of the most important factors of success because their location ultimately determines the current path in traversing the brain. Many different methods have been investigated in order to transfer the TCES waveform energy from the generator 100 to the patient but the best approach has been to apply the TCES signals directly to the head through one frontal cathode electrode 721 and two posterior electrodes 722, 723 near the back of the ears for a total of three electrodes. Variance from these prescribed locations on the head will result in a lower transfer of power to the patient and a far less transfer of useful energy to the patient.

Type of electrodes and material used will maximize the TCES waveform and effect. There are many options for electrodes but the characteristics of the electrodes must be carefully chosen otherwise there is considerable waste of power that can be transferred to the patient. Initially silver foil electrodes were used with a gel that facilitated the energy transfer. Although this approached worked quite well it was inconvenient. It was found that a high quality electrode with a conductive silver layer that is pre-gelled provides adherence and reusability with uniform current distribution and comfortable stimulation. Other types of electrodes commonly used failed to provide the low impedance necessary to have an optimum transfer of power.

Size and shape of the electrodes that provide optimal connection to the patient. The size of the electrode is important because that dictates the amount of energy that can be transferred from the skin into the brain. With the proper electrode material a round electrode with a diameter of 2 inches works well. However, because of the location on the head where the electrode must be connected the round shape is not optimal. For this invention modified electrodes are used. The frontal cathode electrode is round with portions cut out on either side to more fully adhere to the contour of the nose, FIG. 7a. Two different shapes can be used as the posterior electrodes, one in an oval shape, FIG. 7b the other in a crescent or banana shape, see FIG. 7c.

The invention claimed is:

1. A waveform generator for transcutaneous electrical stimulation comprising;
   a power source electrically connected to a logic control,
   the logic control programmed to create a digital TCES waveform,
   the logic control operably connected to a switching circuit,
   the switching circuit operably connected to a first transformer,
   the first transformer, configured to convert the digital TCES waveform to an analog TCES waveform including a high frequency component,
   the first transformer operably connected to a second transformer,
   the second transformer configured to remove a portion of the high frequency component of the analog TCES waveform received from the first transformer to create the desired final waveform,
   an output system operably connected to the second transformer, and,
   the output system including;
      an output control circuitry electrically connected to a plurality of output leads and wherein each output lead is coupled to a respective electrode pad.

2. The waveform generator of claim 1 wherein the power source is alternating current or direct current.

3. The waveform generator of claim 1 wherein the digital TCES waveform is a square wave having $2/3$ positive amplitude and $1/3$ negative amplitude.

4. The waveform generator of claim 1 wherein the digital TCES waveform has net zero voltage.

5. The waveform generator of claim 1 wherein the analog TCES waveform is a shaped wave.

6. The waveform generator of claim 5 wherein the shaped wave is formed when the rate of amplitude gain is progressively decreased as the wave approaches peak amplitude in both positive and negative directions.

7. The waveform generator of claim 1 wherein the first transformer and second transformer include a high permeability ferrite toroid.

8. The waveform generator of claim 1 wherein the digital TCES waveform includes a startup wave, a driving wave and an end wave.

9. The waveform generator of claim 8 wherein the startup wave and end wave are $1/3$ amplitude of the driving wave.

10. The waveform generator of claim 1 wherein the final waveform does not include a direct current component.

11. The waveform generator of claim 1 wherein the plurality of leads comprises three output leads wherein each output lead is coupled to a respective electrode pad.

12. The waveform generator of claim 11 wherein the electrode pads include a nose pad and two posterior ear pads.

13. The waveform generator of claim 12 wherein the nose pad including triangular relief cut outs.

14. The waveform generator of claim 12 wherein the ear pads are one of crescent and banana shaped.

15. A method of using a waveform generator for transcutaneous electrical stimulation comprising;
   providing a waveform generator having,
      a power source electrically connected to a logic control,
      the logic control programmed to create a digital TCES waveform,
      the logic control operably connected to a switching circuit,
      the switching circuit operably connected to a first ferrite toroid transformer,
      the first ferrite toroid transformer configured to convert the digital TCES waveform to a analog TCES waveform including a high frequency component,
      the first ferrite toroid transformer operably connected to a second ferrite toroid transformer,
      the second ferrite toroid transformer configured to remove a portion of the high frequency component of the analog TCES waveform received from the first ferrite toroid transformer to create a desired final waveform,
      an output system operably connected to the second ferrite toroid transformer,
      the output system including;
         an output control circuitry electrically connected to a plurality of output leads wherein each output lead is coupled to a respective electrode pad,
         the electrode pads connected to the output leads including,
            a nose pad, and,
            two posterior ear pads,
   attaching the nose pad to the forehead and intersecting the bridge of the nose of a user,
   attaching each of the posterior ear pads behind and slightly above each ear of the user,
   initiating the power source, and,
      adjusting the output control circuitry to a desired level.

* * * * *